(12) United States Patent
Turin (10) Patent No.: US 11,590,245 B2
(45) Date of Patent: *Feb. 28, 2023

(54) METHOD OF DETECTING PASSIVELY INDUCED RF EMISSIONS FROM SPIN POLARIZED ELECTRONS

(71) Applicant: SPINPOLAR LTD, Buckingham (GB)

(72) Inventor: Luca Turin, Buckingham (GB)

(73) Assignee: SPINPOLAR LTD, Buckingham (GB)

( * ) Notice: Subject to any disclaimer, the term of this patent is extended or adjusted under 35 U.S.C. 154(b) by 0 days.

This patent is subject to a terminal disclaimer.

(21) Appl. No.: 17/540,957

(22) Filed: Dec. 2, 2021

(65) Prior Publication Data

US 2022/0088227 A1    Mar. 24, 2022

Related U.S. Application Data

(60) Division of application No. 17/100,084, filed on Nov. 20, 2020, now Pat. No. 11,191,852, which is a continuation-in-part of application No. 15/683,960, filed on Aug. 23, 2017, now abandoned.

(60) Provisional application No. 62/417,366, filed on Nov. 4, 2016.

(51) Int. Cl.
| | |
|---|---|
| *A61B 5/00* | (2006.01) |
| *A61K 49/10* | (2006.01) |
| *A61B 5/0536* | (2021.01) |
| *A61B 5/145* | (2006.01) |
| *A61B 5/055* | (2006.01) |
| *A61B 5/375* | (2021.01) |
| *A61B 5/0522* | (2021.01) |
| *A61B 5/05* | (2021.01) |
| *G01N 24/00* | (2006.01) |

(52) U.S. Cl.
CPC .............. *A61K 49/10* (2013.01); *A61B 5/055* (2013.01); *A61B 5/0536* (2013.01); *A61B 5/14542* (2013.01); *A61B 5/375* (2021.01); *A61B 5/05* (2013.01); *A61B 5/0522* (2013.01); *G01N 24/00* (2013.01); *Y10T 436/24* (2015.01)

(58) Field of Classification Search
CPC ...... A61K 49/10; A61B 5/375; A61B 5/0536; A61B 5/055; A61B 5/14542; A61B 5/05; A61B 5/0522; Y10T 436/24; G01N 24/00
See application file for complete search history.

(56) References Cited

U.S. PATENT DOCUMENTS 5,263,482 A * 11/1993 Leunbach .............. G01R 33/62
                                                   600/420

* cited by examiner

*Primary Examiner* — Keith M Raymond
*Assistant Examiner* — Adam D. Kolkin
(74) *Attorney, Agent, or Firm* — DP IP Group; Franco De Liguori (57) ABSTRACT

A method of passively detecting radiofrequency (RF) signals spontaneously emitted by a non-equilibrium population of electrons that are spin polarized by flowing through a chiral media during relaxation of the spin polarized electrons to equilibrium at a frequency corresponding to a Zeeman spin-flip energy of the spin polarized electrons under influence of a magnetic field (MF). The MF is applied to the chiral media for a predefined time period to shift a frequency and magnitude of the spontaneously emitted RF signals in line with Zeeman effect. The shifted emitted RF signals is passively detected and stored for medical use applications using a receiver antenna tuned to a resonant frequency of the shifted emitted RF signals.

14 Claims, 6 Drawing Sheets

METHOD OF DETECTING PASSIVELY INDUCED RF EMISSIONS FROM SPIN POLARIZED ELECTRONS

RELATED APPLICATIONS

This application is a continuation of U.S. Non-Provisional application Ser. No. 17/100,084, filed on Nov. 20, 2020, entitled "MEDICAL DEVICE FOR DETECTING PASSIVELY INDUCED RF EMISSIONS FROM SPIN POLARIZED ELECTRONS", now U.S. Pat. No. 11,191,852, issued Dec. 7, 2021, which claims priority of U.S. Non-Provisional application Ser. No. 15/683,960, filed on Aug. 23, 2017, entitled "PASSIVELY INDUCED RF EMISSIONS FROM SPIN POLARIZED ELECTRONS IN LIVING MATTER", which claims the benefit of U.S. Provisional Application No. 62/417,366, filed on Nov. 4, 2016, entitled "PASSIVELY INDUCED RF EMISSIONS FROM SPIN POLARIZED ELECTRONS IN LIVING MATTER", all commonly owned and assigned to the same assignee hereof.

FIELD

The present disclosure relates to techniques for generating, detecting, and measuring passively induced RF emissions from living organisms.

BACKGROUND

A biosignal is any signal in living beings that can be continually measured and monitored. The term biosignal is often used to refer to bioelectrical signals, but it may refer to both electrical and non-electrical signals. The usual understanding is to refer only to time-varying signals, although spatial parameter variations (e.g. the nucleotide sequence determining the genetic code) are sometimes subsumed as well.

Electrical biosignals, or bioelectrical time signals, usually refers to the change in electric current produced by the sum of an electrical potential difference across a specialized tissue, organ, or cell system like the nervous system. Thus, among the best-known bioelectrical signals are:

Electroencephalogram (EEG)
Electrocardiogram (ECG)
Electromyogram (EMG)
Mechanomyogram (MMG)
Electrooculography (BOG)
Galvanic skin response (GSR)
Magneto encephalogram (MEG)

EEG, ECG, EOG and EMG are measured with a differential amplifier which registers the difference between two electrodes attached to the skin. However, the galvanic skin response measures electrical resistance and the MEG measures the magnetic field induced by electrical currents (electroencephalogram) of the brain.

With the development of methods for remote measurement of electric fields using new sensor technology, electric biosignals such as EEG and ECG can be measured without electric contact with the skin. This can be applied for example for remote monitoring of brain waves and heartbeat of patients who must not be touched, and, in particular, patients with serious burns.

Electrical currents and changes in electrical resistances across tissues can also be measured from plants.

Biosignals may also refer to any non-electrical signal that is capable of being monitored from biological beings, such as mechanical signals (e.g. the mechanomyogram or MMG), acoustic signals (e.g. phonetic and non-phonetic utterances, breathing), chemical signals (e.g. pH, oxygenation) and optical signals (e.g. movements).

The signals detected by techniques such as EEG and EKG are due to currents carried by ions, and in particular, the charged particles created by dissolved salts in the human body, mainly $Na^+$, $Ca^{++}$ and $K^+$. As these ions flow across cell membranes, this manifests in fast signaling from one end of a neuron to the other. In an average sized person, the nerves that extend from the spinal cord to the toes are more than a meter long. When a neuron or heart cell "fires", ionic currents briefly flow and their sum total—attenuated by distance and smeared with the activity of all other neurons—reaches the surface of the skull in the form of small and slow waves detectable by an EEG measuring device. The ion currents generated during a single firing event can be as much as 10 nano-amperes. If we were to assume a rough estimate of $10^{11}$ neurons in the average adult, if all these neurons were to theoretically fire at the same time, if we were to add the sum of all the ionic currents generated, this amount would equal approximately one hundred amperes of total peak current.

Despite this, ion currents are dwarfed by other, rather more mysterious and silent currents flowing through each and every cell of our body, and for that matter of every living thing that uses oxygen or another terminal electron acceptor to breathe, including bacteria. These other currents are "electron currents". Electron currents are just as essential to life as ionic currents and play a critical role in cellular respiration.

Cellular respiration is a set of metabolic reactions and processes that take place in the cells of organisms during which biochemical energy from nutrients is converted into adenosine triphosphate (ATP), and then release waste products (mostly carbon dioxide). The reactions involved in respiration break large molecules into smaller ones, releasing energy (induced by electron currents) in the process. Respiration is one of the main ways a cell releases chemical energy to fuel cellular activity. The "powerhouse of the cell" where most of the cell's supply of ATP is produced and used as a source of chemical energy, is the mitochondrion (or mitochondria).

Oxygen plays a key role in the cellular respiration process because energy is released when a molecule of oxygen ($O_2$) combines with four electrons and four hydrogen ions to form two molecules of water ($H_2O$). This chemical reaction is expressed as:

$$O_2 + 4e^- + 4H^+ \rightarrow 2H_2O \qquad \text{eq. (1)}$$

By calculating the amount of oxygen consumed per unit time and turned into water by a living organism over a given period, it is possible to determine the magnitude of the electron currents involved during respiration. A human at-rest consumes approximately 220 mm³ of $O_2$ per gram of tissue per second. This translates into seventy five (75) amperes of total peak electron currents. During peak physical activity, as in extreme aerobic exercising, the human body can release up to 1000 amperes of total electron currents.

While bio-scientists are aware that electron current biosignals exist and the circumstances under which released, to date there is no technique to directly measure and detect such biosignals. One of the reasons is that the biosignals involved in respiration are steady signals and there is no technique for measuring steady biosignals. Furthermore, electron currents flow in all spatial directions within the cell and the organism, and the steady magnetic fields they create cancel each other out.

The electron transport chain function is not independent of what is happening outside the mitochondria in a given cell. The host cell also plays a role. Needless to say, the main function of the electron transport chain is to add two electrons to each oxygen atom and use the difference in potential between the source of the electrons (the cell metabolism) and the sink of the electrons (oxygen) to drive the movement of H+ ions at right angles to the electron flow, i.e. across the membrane of the mitochondrion. This flow of H+ ions in turn is used to make energy. While the adding of four electrons to an oxygen molecule to make two waters is critical for energy to be created, sometimes less than four electrons combine to the oxygen molecule, and this results in the creation of so called "free radicals". In essence, we have oxygen molecules with unpaired electrons.

Free radicals are magnetic in nature, and but for the fact that the electron transport chain ensures that very few are produced, conventional biosignal measuring techniques could, in principle, allow for the measurement and detection of free radicals. In theory, free radicals no less than $10^{11}$ or $10^{12}$ would be required for detection, a number that's too high for current technology.

In very general terms, cells consume the chemical fuel (ATP) produced during cellular respiration while the electricity (electron currents) generated during the process is simply a by-product of that process.

All charged particles experience a force at right angles to their direction of motion when moving in a magnetic field. A peculiarity of electrons is that they feel a force in a magnetic field gradient even at rest and behave like microscopic magnets. Physicists refer to the magnetic property of deflection as "spin". When discussing the behavior of subatomic particles, the rules of quantum physics apply. In this regard, it is misleading to conjure up an image of the electron as a small spinning object since it is not, in the sense of classical physics, a solid object. Rather it is best simply to accept the observed fact that the electron is affected by magnetic fields. If one insists on the image of a spinning object, then real paradoxes arise; unlike a tossed softball, for instance, the spin of an electron never changes in a graded fashion, and it has only two possible orientations.

It has been suggested that cellular organisms undergo a change in observed total spin content. In an article by Turin et. al., (titled. "Electron Spin Changes During General Anesthesia in Drosophila, Proc. Natl. Acad. Sci., USA, Aug. 26, 2014, vol. 111 no. 34, E3524-33), incorporated herein by reference, Applicant opined that the change in observed spin may be attributed to electrons undergoing spin polarization. To prove the premise, electron polarization measurements were previously employed to deduce that electrons traversing chiral materials (i.e., the protein matter that makes up mitochondrial matter in a living organism) do in fact become spin-polarized in the direction of motion, with spin polarization reaching 80% in thin layers of some biological materials.

Given electron currents cannot be directly detected, magnetic resonance was employed merely to establish findings of measurable changes in magnetic field (MF) response properties before and after anaesthetizing fruit flies (*Drosophila*) under evaluation. Fruit flies are commonly used in such tests due to the nature and similarity of biosignal response to other animal living organisms. It was concluded that the MF changes in magnetism were attributed to electrons residing on the carbon atoms of an unknown molecule or molecules.

It is desirable to be able to take advantage of the discovery that electrons involved in the generation of electron currents in cell organisms are spin polarized.

It is further desirable to be able to provide medical diagnosis, imaging and other commercial applications which are based on the non-invasive and/or non-destructive detection and/or measurement associated with the spin polarized nature of electrons in cell organisms, and in particular, respiring organelles generally.

SUMMARY

The present disclosure is directed to a novel medical device that utilizes, for diagnosis and other medical uses, the detection of emitted radiofrequency (RF) signals experimentally shown as spontaneously emitted by a non-equilibrium population of spin polarized electrons in chiral media during their relaxation to equilibrium. The emitted RF signals correspond to the Zeeman spin-flip energy of electrons under the influence of a magnetic field (MF), which in the absence of an external MF are too difficult to detect. Using a larger MF shifts the low energy, low frequency RF emission of spin polarized electrons to a higher RF power emission wave characterized by a fixed resonant frequency. The detection of these higher RF power emissions is relatively easy using conventional MF magnet sources and antenna receiver technology. The present disclosure relates to medical diagnosis devices and techniques associated therewith to facilitate the detection and measuring of emitted RF waves in living cell organisms characterized by chiral matter the electron transport chain of which includes spin polarized electrons.

DETAILED DESCRIPTION

The word "exemplary" is used herein to mean "serving as an example, instance, or illustration." Any embodiment described herein as "exemplary" is not necessarily to be construed as preferred or advantageous over other embodiments. It is to be understood that the terminology used herein is for purposes of describing particular embodiments only and is not intended to be limiting. The defined terms are in addition to the technical and scientific meanings of the defined terms as commonly understood and accepted in the technical field of the present teachings.

As used in the specification and appended claims, the terms "a", "an" and "the" include both singular and plural referents, unless the context clearly dictates otherwise. Thus, for example, "an apparatus" or "a device" includes one apparatus or device as well as plural apparatuses or devices.

In the following detailed description, for purposes of explanation and not limitation, representative embodiments disclosing specific details are set forth to provide a thorough understanding of the present teachings. Descriptions of known systems, devices, materials, methods of operation and methods of manufacture may be omitted to avoid obscuring the description of the example embodiments. Nonetheless, systems, devices, materials, and methods that are within the purview of one of ordinary skill in the art may be used in accordance with the representative embodiments.

A possible measurement method was provided by the discovery that electrons flowing through chiral media are spin polarized. What does this mean? Every electron is a tiny magnet. In atoms, the electrons are always arranged in pairs such that the magnetism of the electrons, one "up" and one "down" (these directions are set by the direction of an external magnetic field) balances out such that the atom has no overall magnetism. Even in a metal wire, where electrons carry the current, equal numbers of up and down electrons ensure the wire has no built-in magnetism.

It has recently become technologically feasible to create electron currents in which the magnetism, or "spin" of the electrons does not cancel out. This is typically achieved by making electrons flow through a permanent magnet which impedes the flow of electrons oriented against its own magnetic field. Modest imbalances of spin in the current can be achieved, and they have created a novel field of low-energy technology called spintronics.

The reason spintronics is interesting is that the energy involved in making a spin change from up to down is very small, and linearly proportional to the magnetic field the electron finds itself in. To put in context of current technology, the energy change of electrons in current electronics is of the order of 1 electron-volt, or eV. Thermal energy at room temperature is 0.03 electron volts. Spin energy in the strongest magnetic field anyone is likely to be exposed to, the 3 Tesla field inside an MRI machine, is ninety times smaller than thermal energy.

Creating spin polarized currents is far from easy using man-made materials. It appears, however, that life has found a way to do so which is enormously more efficient. If in fact the hypotheses hold true that electrons travelling through proteins and other biological media become almost completely spin polarized, it stands that most of the electrons in the mitochondrial electron transport chain will also be spin polarized as well.

Unfortunately, as has been explained, today's measurement and detection instruments are designed to detect the magnetism of electrons (electron spin resonance machines). The fundamental principle is that by hitting electrons with radiofrequency waves, and specifically microwaves of a desired optimum frequency corresponding to the local magnetic field, electrons jump from a lower energy spin state to a higher energy spin state and in the process absorb the incident microwaves. The absorption characteristics are analyzed, and certain medical conclusions drawn depending on the device.

In the case of spin polarized electrons, we are talking about electrons that are already in a higher state and hence there is no absorption affect since there is no "jumping" from one state to a higher state.

Applicant has deduced nevertheless that the spin polarized electrons do in fact emit radiowaves and set out to detect and measure these waves. A testing environment utilizing fruit flies was used to prove the principle, as described in greater detail below.

In accordance with an exemplary embodiment, a medical diagnosis device is provided to facilitate the detection and measuring of emitted RF waves in living cell organisms characterized by mitochondria, the electron transport chain of which includes spin polarized electrons.

In accordance with a further exemplary embodiment, techniques are provided involving the detection and measuring of emitted RF waves in living cell organisms characterized by respiring organelles, the electron transport chain of which includes spin polarized electrons.

In yet a further exemplary embodiment, the techniques involve non-resonant imaging.

Testing Environment

It is known that polarized electrons from spintronic devices and arising from certain highly specialized chemical reactions are capable of RF emission, and specifically, so-called "stimulated emission." Stimulated emission is emission of radio waves in response to radio waves themselves. A resonating cavity is employed in which radio waves slosh back and forth eliciting more radio waves as they bounce to and fro from the end walls. Eventually, the intensity is high enough that it becomes detectable. This only works if the medium in which the radio waves travel is not strongly absorbing. If it is, the resonating cavity merely increases absorption by increasing the effective length radiowaves travel, and therefore absorption. By contrast, spontaneous emission merely requires the radio waves to travel once the distance separating the location in the interior of the tissue where the waves are generated from free space.

Consequently, despite conventional wisdom, a different approach was taken: spontaneous emission without resonance. In spontaneous emission, there is no "stimulating" chemical reaction as such. Instead, the focus is on applying a MF and looking at the electron spin change.

Conventional wisdom until now would have led one not to consider spontaneous emission because as electron spin jumps from high to low, spin changes are believed to be undetectable because they will mostly occur by thermal processes that do not cause emission of radio waves.

Figure 1:
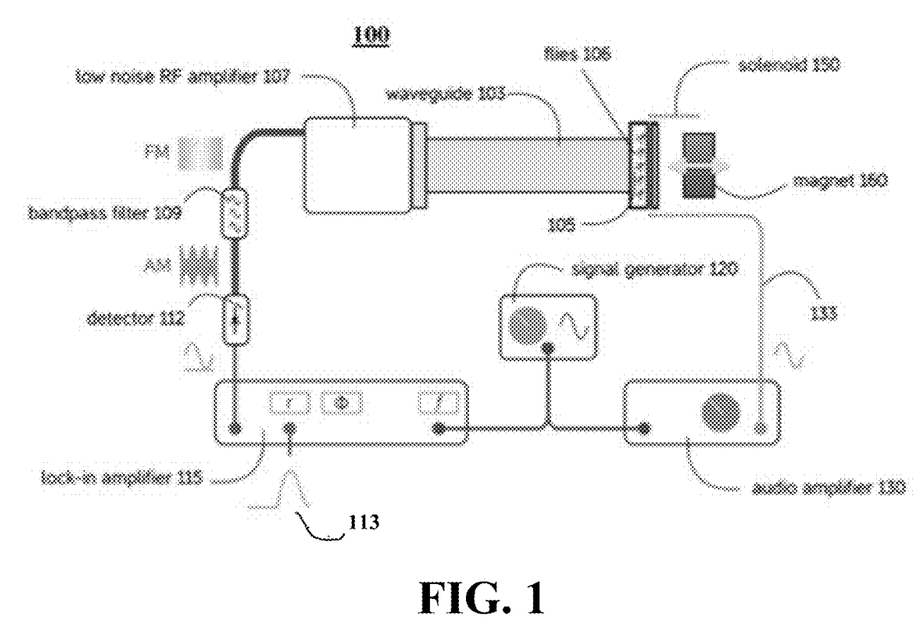
FIG. 1 is a high-level block diagram of a laboratory setup, in accordance with an exemplary embodiment, for detecting and measuring emitted RF waves in living cell organisms the electron transport chain of which includes spin polarized electrons.

FIG. 1 is a high-level block diagram of a laboratory setup 100, in accordance with an exemplary embodiment, for detecting and measuring emitted RF waves in living cell organisms the electron transport chain of which includes spin polarized electrons.

Setup 100 includes waveguide 103 defined at one end by a chamber 105 which is configured to contain a plurality of fruit flies 106. The opposite end of waveguide 103 is coupled to a low noise RF amplifier (LNA) 107. The output of LNA 107 in turn feeds into bandpass filter (BPF) 109, which output is fed into detector 112. The output of detector 112 is biased by a lock-in reference signal 113 generated by lock-in reference signal generator (LRSG) 115. A signal generator (oscillator) 120 generates the main reference signal that feeds into both LRSG 115 and also audio amplifier 130. Audio amplifier 130 converts the received main reference signal to an oscillating current signal 133 and transmits same to solenoid 150. The field of solenoid 150 is simultaneously summed to the field of permanent magnet 160.

Referring to FIG. 1, the test is initiated by placing fruit flies 106 into chamber 105, which chamber is part of a waveguide 103 (or similar rectangular-section metal-walled pipe) configured to propagate radio waves of a particular range of frequencies.

Waveguide 103 acts as a radiofrequency "darkroom" by preventing radio waves other than those entering from cavity 105 from entering. Waveguide 103 also serves to guide emitted radio waves from cavity 105 to the opposite end connected to LNA 107.

In a preferred scenario, LNA 107 is a high-sensitivity C-band satellite TV receiver tuned to operate at 4 GHz. C-band receivers are extremely popular which allows for this experiment to be conducted without any special, expensive, or difficult to obtain components. Waveguide 103 is likewise tuned to a matching frequency.

To emit at a frequency that will be transmitted by waveguide 103 and picked up by LNA 107, flies 106 are immersed in a magnetic field of appropriate magnitude. Quantum mechanics dictates that a free electron, or an unpaired electron attached to a carbon atom, has a resonant frequency of 28 gigahertz per Tesla (1 Tesla=10,000 gauss). In the present example, an appropriate magnitude is 1600 gauss. A steady 1600 gauss magnetic field carrier wave is supplied by permanent magnet 160. To increase detection sensitivity, an oscillating current signal 133 is fed to solenoid 150 to modulate the magnetic field and hence the frequency of the radio signal.

LNA 107 is designed to detect the RF emissions signal caused by exposing spin polarized electrons in the mitochondrial matter of the flies to sum of the 1600 gauss MF and the MF signal generated by solenoid 150. The output signal from the LNA 107 is fed to a bandpass filter centered on the frequency caused by the permanent magnet 160 to turn frequency modulation into amplitude modulation. The envelope of the amplitude modulated (AM) signal exiting filter 109 is demodulated by a zero-bias detector diode 112 and turned onto a low-frequency signal at the oscillating frequency of signal 133.

RF Generation

Figure 2:
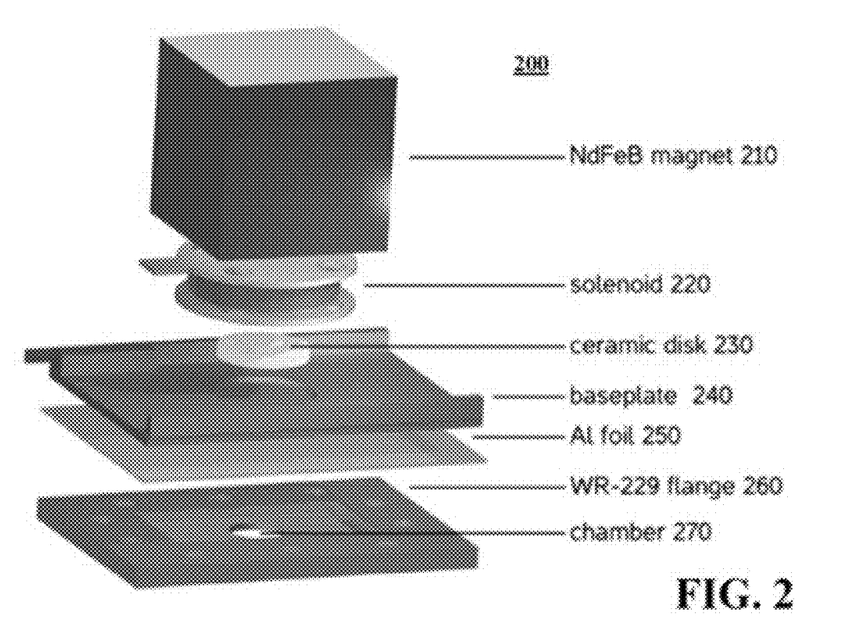
FIG. 2 is an exploded actual component view diagram of a partial section of the waveguide, solenoid, magnet and related intermediate components in accordance with the laboratory setup of FIG. 1.

FIG. 2 is an exploded actual component view diagram of a partial section of an assembly 200 comprised of waveguide, solenoid, magnet, and related intermediate components in accordance with laboratory setup 100.

Referring to the exploded review of FIG. 2, illustrated is a NdFeB type magnet 210, solenoid 220, ceramic disk 230, baseplate 240, aluminum (Al) foil 250, waveguide flange portion 260, and waveguide chamber 270. The waveguide sections shown are part of waveguide 103 in FIG. 1, which waveguide is a WR-229 type waveguide 75 cm in length.

For ease of handling, waveguide 103 has a 90-degree bend at one end which forms waveguide flange portion 260 as shown. The open-end is upward-pointing and horizontal in the direction of solenoid 220 (150) and magnet 210 (160). A Teflon partition transparent to RF is inserted into waveguide 103 to produce chamber 270 (105) which is approximately 3 mm deep.

Waveguide 103 is a closed sub-assembly constructed of 3D-printed parts made of acrylonitrile butadiene styrene (ABS) of appropriate size. The subject sub-assembly couples end baseplate 240 and solenoid spool 220 together with thermally insulating disk 230 and a sheet of conducting metal foil 250.

Assembly 200 serves two purposes. The first purpose is for to the foil 250 to provide an RF-reflecting surface terminating the waveguide. Here, the ABS is lined with aluminum foil to make electrical contact with the waveguide flange. The second purpose is to allow both a steady and a time-varying magnetic field to reach the flies in the cavity.

Constant Magnetic Field

For low-cost construction and ease of replication, a 50×50×50 mm NdFeB (grade N52) permanent magnet is used. Magnet 210 (160) has a surface field (measured with a Trifield GM2 gauss meter) of approximately 6000 Gauss. On-axis, the field 25 mm away from the magnet face is ≈1600 gauss. Magnet 210 (160) is positioned in the vertical axis by an MM-3 micropositioner with 50 mm travel.

Variable Magnetic Field

Lock-in detection is a well-known RF principle to improve signal-to-noise ratio. The choice of frequency is limited above by eddy currents and attendant attenuation, which in aluminum foil is of the order of 8 dB at 10 kHz. The lower frequency limit is set by signal-to-noise ratio and the desired response time of the lock-in. A typical ratio of lock-in signal frequency to output (inverse) time-constant, is of the order of 100. The ABS part terminating the waveguide incorporates an 8 mm high spool with an inner diameter 30 mm.

Experimental results established that a few hundred turns of 0.64 mm magnet wire could generate a variable field at audio frequencies (typically 1 kHz) of about 100 gauss without heating beyond 35 C, the upper temperature limit that the flies can stand in the chamber below.

Again, to facilitate replication, an inexpensive class-T audio (Winsome Mouse) amplifier 130 is used, incorporating a Tripath chip as a current source. The amplifier is driven by digital sinewave generator 120, which also provides a TTL reference signal to lock-in amplifier 115.

RF Detection

LNA: The WR-229 waveguide 103 will pass frequencies between 3.22 and 4.9 GHz. RF in the waveguide cavity is detected by a satellite C-band Low-noise Block Converter 107 such as LBC device NJS8488U manufactured by New Japan Radio Corporation. The LNA is tuned to the satellite downlink C-Band and was chosen for its low cost and low noise temperature of ≈20K. This is a heterodyne device that mixes an input signal in the range 4.5 to 4.8 GHz, corresponding to magnetic fields of 1610 and 1710 gauss, with an internal (LO) oscillator at 5.6 GHz to give an output $f_{LO}-f_{signal}$ between 960 and 1260 MHz. The LNA is powered by a "phantom" supply, in which the core conductor of the coaxial output feeds the amplifier with nominal 24 V, 250 mA via a bias-T AC-coupled to the rest of the circuit. Commercially available bias-Ts have a secondary pole around 10 MHz to pass control signals. This was found to cause unwanted pickup of the AC magnetic field, and a custom-made Bias-T (Actox corporation) is used with a single pole at 2 GHz.

FM-to-AM Conversion and Detection

A varying magnetic field at the generating end will result in a frequency modulated RF signal. The lock-in amplifier requires a demodulated, rectified, and low-pass filtered signal. Accordingly, the output of the LNA is fed to an RF bandpass filter 109 with a center frequency of 1.15 GHz and width≈60 MHz, and from there to a zero-bias Schottky diode detector (Krytar 301A) 112. To improve the small-signal rectification by expanding the signal further into the nonlinear part of the Schottky diode characteristic, a second 30 dB gain stage (Mini Circuits ZKL 2+) is interposed between filter and detector. The demodulated and rectified signal is fed to the input of a Stanford Research SR-530 lock-in amplifier 115. Unless otherwise specified, all signals were recorded in modulus-phase (r-phi) mode. The output from the lock-in amplifier is recorded with a 16-bit USB digital oscilloscope (Picoscope 4262).

Calibration

To calibrate the instrument, a USB RF generator (Windfreak Technologies SynthHD) is used in FM mode to generate test signals. At 4650 MHz, the midpoint of the LNA frequency range, the RF generator allows for signal attenuation down to −40 dBm. A 30 dB SMA attenuator provided a CW signal of −70 dBm, or ≈100 pW. The 300 MHz of passband of the LBC corresponds to an AC magnetic field modulation of 2110 gauss. At 10 MHz FM modulation the measured signal at the lock-in is 1600 µV, or approximately 24 µV/fW.

Experimental Setup

The biological sample is held in a shallow chamber at one end of a waveguide, bounded on one side by the waveguide end-plate and on the other side by a partition inside the waveguide made of a thin sheet of material transparent to radio waves. At the other end of the waveguide is a microwave amplifier. The amplifier is demodulated by a zero-bias detector diode D passed through a band pass filter and fed to the input of a lock-in amplifier. The magnetic field is made up of two components:

(i) a steady magnetic field produced by a Nd—Fe permanent magnet with a surface field of the order of 0.6 Tesla. The magnet can be moved in an out with respect to the waveguide to vary the steady magnetic field in the sample chamber; and (ii) an oscillating magnetic field produced by a copper wire solenoid driven by an audio amplifier, itself controlled by a sinewave generator. The output of the sinewave generator also goes to the lock-in, providing the lock-in reference signal. The output of the lock-in amplifier is proportional to the amplitude modulation of the microwave signal by the oscillating magnetic field.

Results

The radiofrequency detection method described above uses standard-issue, off-the-shelf devices. The proposed experimental setup has never been employed to measure RF emissions where the source of the RF emissions are the living organisms. The experimental setup provides clear evidence that 4 GHz radio waves are emitted by the flies under the subject test conditions.

Figure 3:
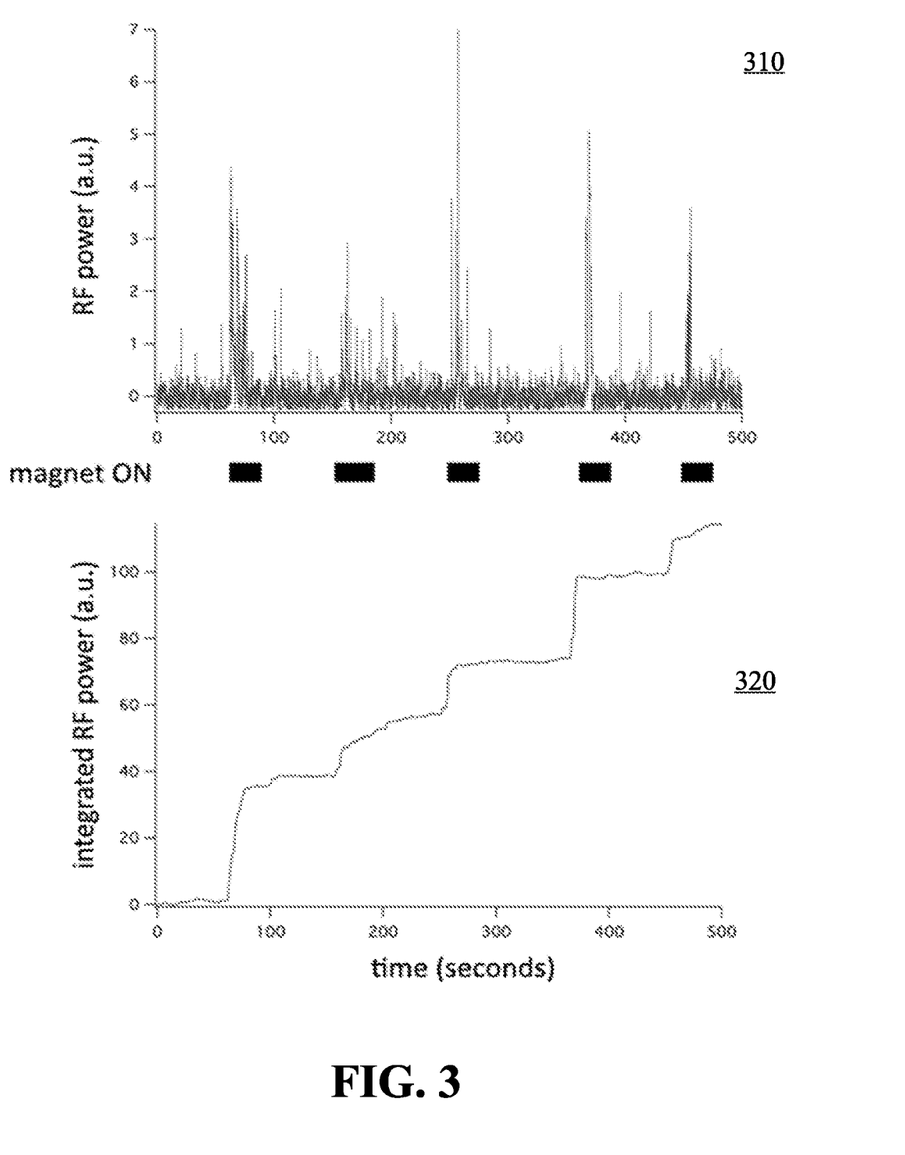
FIG. 3 is a graphical representation of experimental results in accordance with an exemplary embodiment.

FIG. 3 is a graphical representation of the representative experimental results. Upper trace 310 shows lock-in amplifier 115 output—expressed along the y-axis and measured in arbitrary units (a.u.) of detected emitted RF power—versus time (in seconds) along the x-axis. The parameters displayed are modulation frequency 3 kHz, variable field amplitude 20 gauss, lock-in time constant 100 msec. When permanent magnet 210 (160) is brought close enough to the preparation for the chamber to be in a magnetic field corresponding to the Zeeman frequency at ≈4 GHz, i.e., approx. 1600 gauss, bursts of RF (see inset 230, 240) are recorded. The trace (below) 320 shows integrated power accumulation when the magnet is on and no activity when the magnet is off during the interval of trace (i.e., 500 seconds as in the upper trace).

Figure 4:
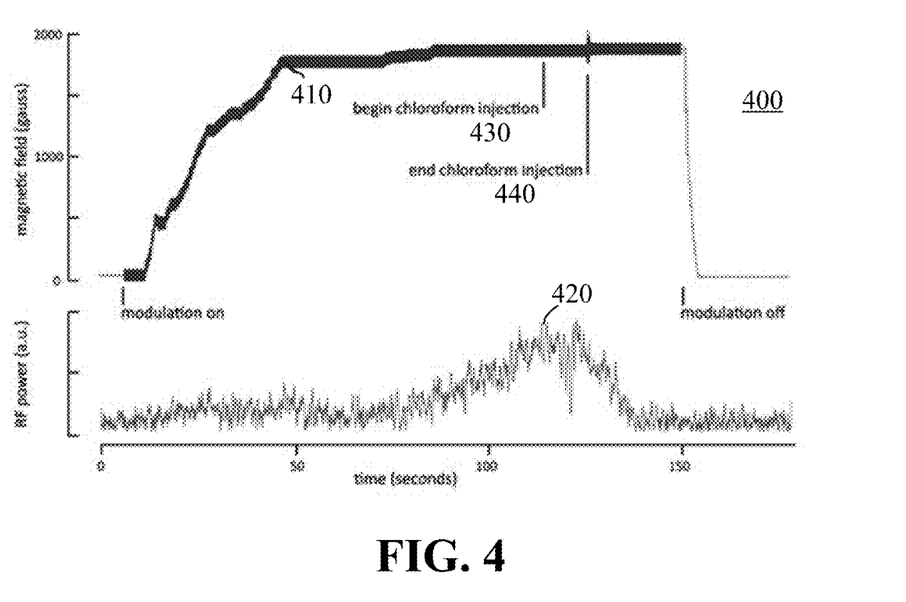
FIG. 4 is a graphical representation showing effect of chloroform on RF emission in accordance with an exemplary embodiment.

FIG. 4 is a graphical representation 400 showing effect of chloroform on RF power emission. Upper trace 410 displays effect of an applied magnetic field (y-axis) versus time (x-axis) while lower trace 420 is displays RF power (y-axis) over same period (x-axis)). As can be seen, the magnetic field is increased from zero to 2000 gauss during a representative recording which is shorter than a few minutes. Before the chloroform is introduced to the flies, the emitted RF power from the flies that is detected (measured in arbitrary units) increases. Once the chloroform is introduced and fully takes effect—i.e., chiral activity ceases or slows down—RF emitted power becomes negligible to indicate a correlation between RF emitted power and cellular activity. When chloroform is introduced to the chamber (represented by 430-440), there is a transient perturbation of the RF signal followed by a return to baseline without change in the magnetic field.

While the experiment was conducted with respect to fruit flies, it should be appreciated that all respiring organisms from bacteria to man will likely show the same radio wave emission, insofar as it is linked to respiration which is a universal mechanism in life.

Likewise, while the laboratory test setup aimed at detecting RF emission patterns associated with fruit flies, the principal test environment may be easily scaled to large scale commercial medical diagnostic equipment designed to test humans, large animals, as well as plant organisms. Larger magnets, RF emission tunneling techniques, and like devices may however be necessary depending on degree of scale up.

Figure 5:
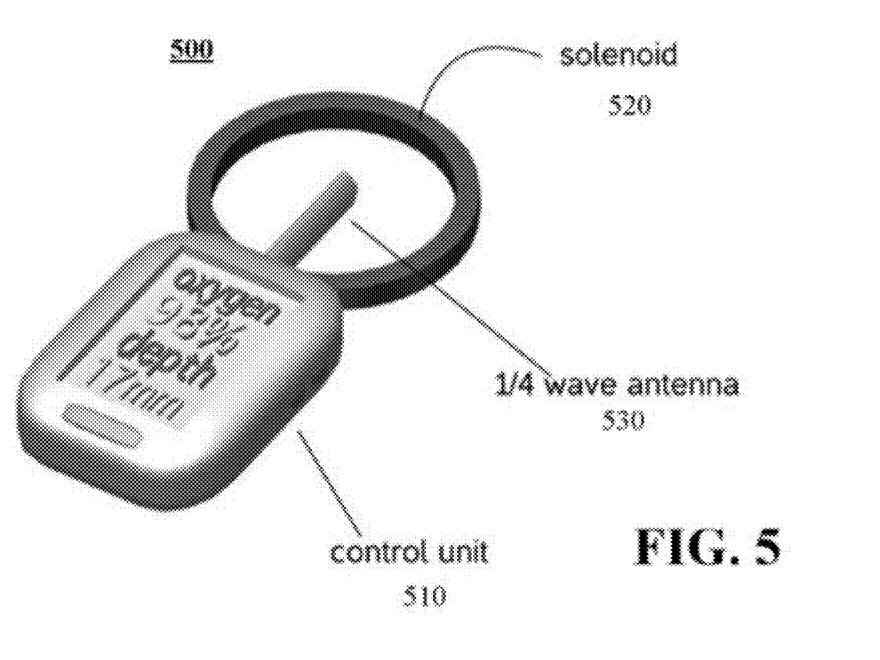
FIG. 5 is a new design for a handheld device constructed in accordance with exemplary embodiment configured to detect and measure emitted RF waves in living cell organisms characterized by respiring organelles, the electron transport chain of which includes spin polarized electrons.

FIG. 5 is a new design for a handheld device 500 constructed in accordance with exemplary embodiment configured to detect and measure emitted RF waves in living cell organisms characterized by respiring organelles, the electron transport chain of which includes spin polarized electrons.

Figure 6:
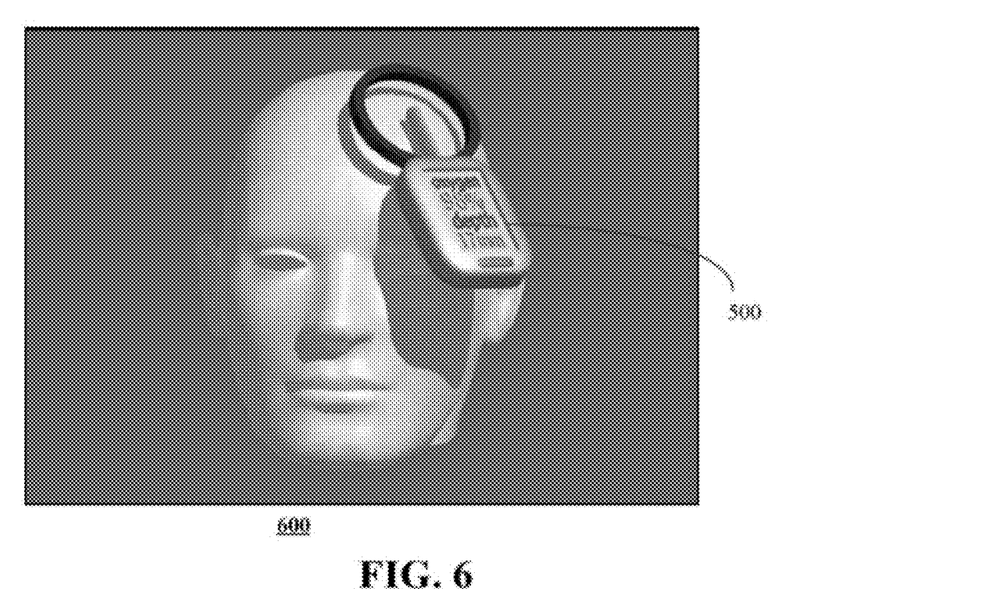
FIG. 6 illustrates a use approach of the handheld device in FIG. 5.

FIG. 6 illustrates a use approach of handheld device 500 in FIG. 5.

Referring to the device of FIGS. 5 and 6, the proposed handheld device 500 comprises a control unit 510, a solenoid 520, and quarter-wave (¼) wave antenna 530.

Control unit 510, in turn, includes a battery (not shown) and sized and configured to power an integrated electronics assembly (also not shown). In an example implementation, solenoid 520 is approximately 6 cm in diameter and defined by an appropriate number of turns of copper wire. Quarter wave (¼) antenna is a straight wire antenna of appropriate dimension (3-4 cm long). Handheld device 500 is designed to generate a pulse of magnetic field a few tens of milliseconds long and of approximately 4000 gauss in the center of solenoid 520. This pulse is low frequency (LF) modulated by about 100 gauss at a few kHz.

Antenna 530 is tuned to detect EM fields in a narrow range between 2 and 4 GHz. A phase-sensitive detector is coupled to the antenna and phase synced to the LF modulated pulse.

Prior to measurements being taken, calibration may be necessary. In this regard, calibration may involve detecting and measuring dissolved oxygen saturation percentages and comparing the results to measurements taken by conventional oxymetry devices.

Figure 7:
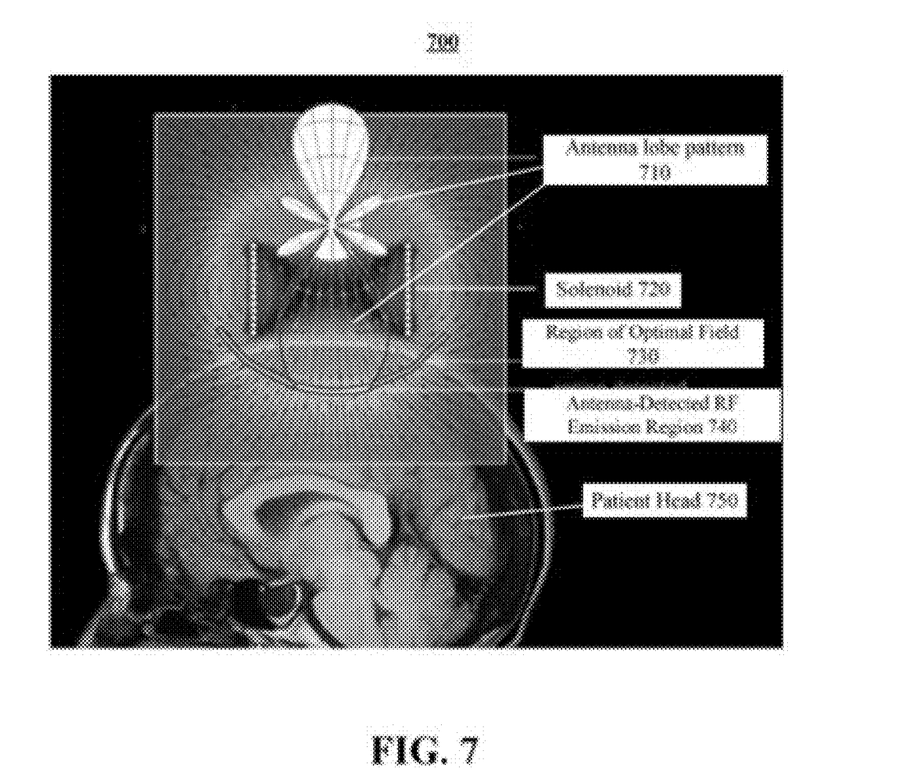
FIG. 7 illustrates flux and MF effects induced by the handheld device when placed on a human head and powered on to radiate desired MF about and into a region of optimal field measurement and detection.

FIG. 7 illustrates flux and MF effects induced by handheld device 500 when placed on a human head and powered on to radiate desired MF about and into a region of optimal field measurement and detection.

In the example embodiment, solenoid 520 is configured to generate an MF of around 28 GHz/Tesla at the surface where the solenoid touches the outermost skin layer of our patient's head. As the MF induced flux from solenoid extends deeper into the skin, flux disperses. At 25 mm, flux (MF) strength is only around 1610 gauss. By powering up our quarter wave antenna to propagate an MF field of around 4 GHz, it will act as a transponder of detected RF at this 25 mm depth.

As we have already established by our experimental setup, chiral matter will cause spin polarized electrons in relevant living organism cells to jump to a higher state, during which transition the electrons acquire energy if subjected to an MF field. When electrons exit a chiral medium, the electrons will eventually settle down and reach an equilibrium state. During the transition to equilibrium, any electrons that have had to transition from this higher state will—in the process of transition—release this extra energy.

As we have theorized and proven experimentally, only those spin polarized electrons at a higher state that acquired energy (due to the incident MF field reaction) will be forced to release this energy. When this extra energy is released, it is released as photonic energy, in other words, in the form of an emitted RF wave of known characteristics.

As such, given that RF energy is detectable and its characteristics known, it is readily possible—using an appropriate antenna receiver tuned to resonate at the known resonating frequency of the emitted RF wave—for this energy to be detected and measured.

In the implementation approach associated with handheld device 500, quarter wave antenna 530 acts as the resonating antenna/receiver. By tuning to the antenna to the applicable resonant frequency and perhaps using appropriate beam forming mechanisms to focus the antenna radiation pattern to optimally match the desired depth at which the photonic bursts are expected to occur, battery consumption, accuracy and measurement robustness and efficiency can be realized.

Assuming appropriately tuned and calibrated, control unit 510 (using conventional receiver circuitry methodologies) will isolate and sense only the signal from the desired depth of 25 mm, which corresponds to the depth at which the solenoid induces sufficient Gaussian MF effect to cause spin polarized electrons at the specific position (depth) to jump.

In the exemplary embodiment, control unit 510 includes a display which shows the depth at which readings were taken. As explained, this depth is variable depending on the strength of the solenoid MF field, the diameter and/or design of the solenoid and other factors.

The display may also indicate oxygenation levels. Since we are talking about causing spin polarized electrons to jump in state, and specifically spin polarized electrons associated with respiring organelles in living cells, there may be a direct correlation to oxygen levels, and oxygenation in particular. Accordingly, once calibrated, our device 500 may be easily operated as an oxymetry device.

Control unit 510 may be configured or pre-programmed to apply a series of readings at different depths by varying the MF produced by the solenoid as well as the radiation pattern and tuning resonance of the antenna.

One skilled in the art would appreciate that there are many different ways to generate MF fields and radiation patterns to increase the depth distance of measurement, accommodate or avoid obstructions that may interfere with measurements and detections, impose practical restrictions and other problems. For example, handheld device may be configured to change in diameter or thickness. In another scenario, handheld device 500 is sized and adapted to accommodate different size solenoids and/or antennas. The antennas may be mechanically integral with the solenoid or independent. In the case of interchanging solenoids or other parts, the control unit may be adapted to automatically identify characteristics about a connected part and calibrate itself for use accordingly.

In another scenario, device 500 may employ or include a wall powered, solar-powered, or other equivalent power source.

Also, device 500 includes a microprocessor, microcontroller, DSP or like central processing and control means, to facilitate processing, network broadcasting, display, storage and/or printing of measured information.

In addition, device 500 can be coupled to other peripherals, including tablets, mobile devices, patient monitoring and information collecting terminals, and the like.

It should also be appreciated that the present application has wide application in imaging type applications and can readily be adopted to perform functions such as those associated with functional MRI imaging. The only difference between conventional imaging techniques and the presently proposed approach is that the former maps the brain and other tissue (and other matter) using magnetic resonance, the principles of which have been discussed in the background, and which require large magnets and high cost to deploy, while the present approach achieves a similar result from similar images collected in a manner which require significantly smaller magnets, at reduced cost, and equipment size and complexity.

Figure 8:
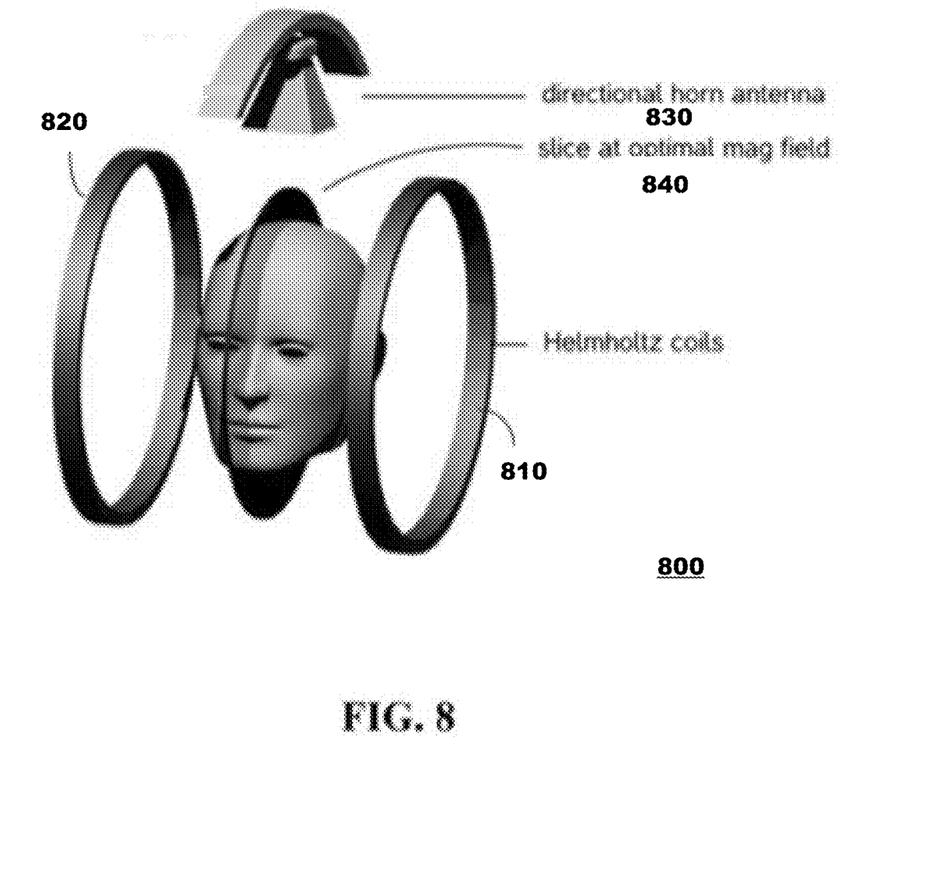
FIG. 8 is a graphical illustration of the principle of varying the MF produced by coils and resonance tuned antenna radiation for use in imaging applications in accordance with an exemplary embodiment of the present invention.

FIG. 8 is a graphical illustration 800 of the principle of varying the MF produced by coils and resonance tuned antenna radiation for use in imaging applications in accordance with an exemplary embodiment of the present invention.

Referring to FIG. 8, two Helmholtz coils 810, 820 are shown disposed a fixed distance from a patient's head. A directional horn antenna 830, or the like, is movably positioned in relation to the patient head to allow one or more sectional images 840 to be taken.

The coils 810, 820 and antenna 830 are coupled to appropriate mechanisms the aim of which is to transport the images to receiver circuitry (not shown) coupled to an imaging computing and processing system. Image processing and image processing equipment are well known techniques and outside the scope of the present application. It is believed that one skilled in the art of imaging medical technology equipment would readily know and appreciate how to modify such equipment to take advantage of the methodologies proposed herein.

Figure 9:
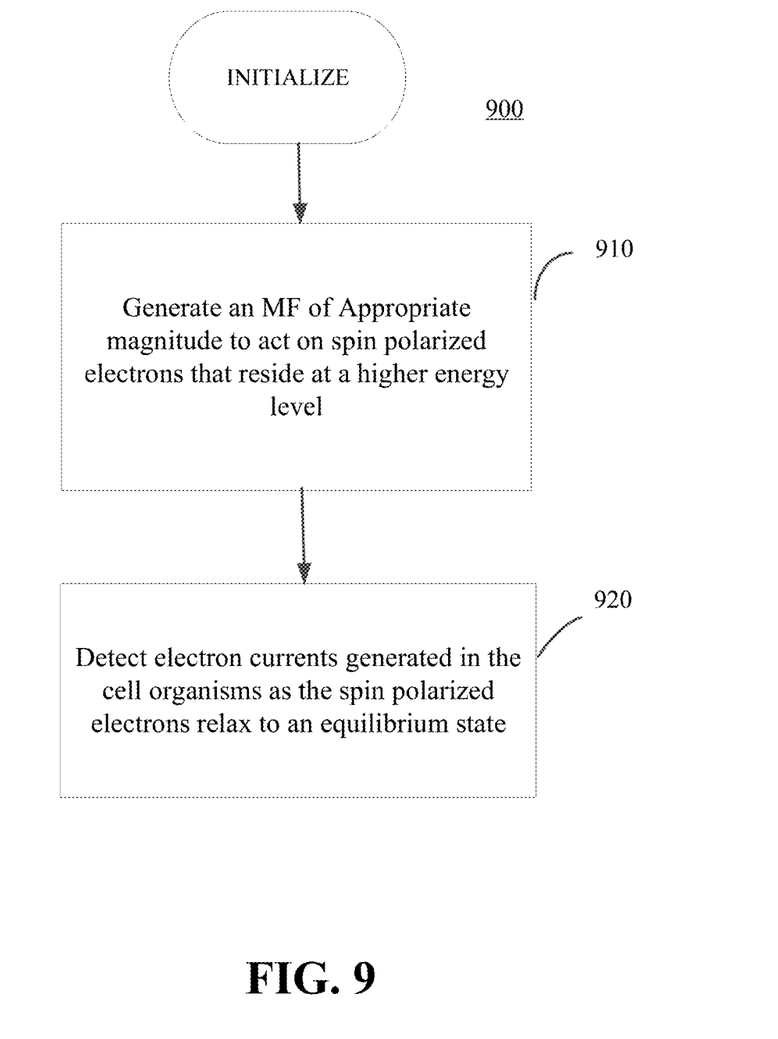
FIG. 9 is a high-level operation flow chart illustrating the methodology of varying MF from magnets, solenoids, coils or the like to facilitate detecting and measuring, using resonance tuned antenna radiation, RF emissions from spin polarized electrons for medical applications in accordance with an exemplary embodiment.

FIG. 9 is a high-level operation flow routine 900 illustrating a methodology of varying MF from magnets, solenoids, coils or the like to facilitate detecting and measuring, using resonance tuned antenna radiation, RF emissions from spin polarized electrons for medical applications in accordance with an exemplary embodiment.

Flow routine 900 is executed by a medical device configured to detect electron currents generated at a desired region of known depth and constituted by living cell organisms characterized by respiring organelles. More particularly, these respiring organelles have an electron transport chain which includes spin polarized electrons.

In accordance with an exemplary embodiment, routine 900 comprises a first step 910 that involves generating an MF of appropriate magnitude to act on the spin polarized electrons that reside at a higher energy level. In a second step, (920), there is detection of the electron currents that are generated in the living cell organisms (and constituted by associated RF emissions) as the spin polarized electrons relax to an equilibrium state. The detecting of the electron currents is achieved using, for example, a receiver to detect an RF wave tuned to a frequency that is proportional to the magnitude of the MF at the fixed depth. This receiver would normally include an appropriately sized antenna and may be a directional antenna with beam forming characteristics.

In accordance with an alternate exemplary embodiment, the medical device includes the ability to vary the MF to cause the spin polarized electrons of living cell organisms to reside in a different energy state at a different region. In this regard, appropriate circuitry is provided to tune the antenna as a function of the currently selected MF magnitude and the desired depth reading.

In an alternate exemplary embodiment, interchangeably replaceable components make it possible to (i) expand the range of MF magnitudes that can be generated, and/or (ii) expand the RF emission characteristics and at different depths that may be detected by antenna components.

Obvious additional experiments are needed to prove the results on for example mice and humans. In the case of mouse tests, it may be appropriate for example to shield from radiofrequencies using a Faraday cage, as well as to use large coils to achieve a steady magnetic field in and around the mouse, and an antenna of the appropriate size to detect the radio waves. Lock-in detection would likely still be useful.

For human experiments, different device implementations are envisaged. One such device is a further portable device (hand-held) containing a permanent magnet and a coil and configured to probe radio wave emission from a small volume below the coil. Another approach is for a device capable of accommodating the head of a person to measure radiowave emissions from the brain area, other than the imaging implementation shown. A third approach calls for a large sized device designed for full-body measurements.

In all instances, the magnetic fields required are an order of magnitude smaller than those used in, for example, MRI imaging applications. By reducing the magnetic field levels required for imaging, both the overall costs and dimensions of conventional measuring machines can be scaled down drastically. This has the potential of revolutionizing the future of medical imaging and related diagnosis.

For imaging purposes, in one scenario, the equipment will need to be configured to apply different magnetic field values for different sections of a live specimen under evaluation. Each section will emit at its corresponding different radio frequency. By analyzing the results on a frequency-by-frequency basis and looking at multiple related sections at once, it is possible to diagnose medical abnormalities, identify neuropathies, and a variety of medical conditions generally.

The experimental fruit fly setup is fundamental to large scale medical diagnosis of human tissue as it is based entirely on the use of microwave emission, not absorption by biological tissue. Microwave ovens work at a technologically convenient frequency of 2 GHz. With that said, lower frequencies travel better inside tissue. For example, 1 GHz RF signals correspond to a modest magnetic field exposure of approximately 400 gauss, considered ideal for testing biological tissue.

As far as the steady fields generated by the magnet, it has been proven that MFs as high as several Tesla have very little effect on living tissue, and in any case, no harm has even been documented.

As far as the variable magnetic field, this is at very low frequency (a few kilohertz) and intensity (a few tens of gauss) and also poses no harm.

As far as regulatory requirements, the proposed techniques for detecting RF emissions of spin polarized electrons are all performed in a passive manner. In other words, there is no power source that acts to introduce external energy to excite atoms with an aim at detecting RF or MF response changes induced by the energy introduced. In the proposed approach, the machine is a sourceless device and deposits virtually no power (aside from the tiny effect of the oscillating small magnetic field) into the preparation. All the power for the emission of radio waves comes from the living organism itself.

The proposed approach is a novel technique for detecting and measuring a new type of biosignal never before used to diagnose the condition of biological tissue (and also possibly plant cell organisms to the extent the latter are shown to exhibit or possess spin polarized electrons in the same or similar way as in chiral matter).

The proposed approach is most akin to applications commonly associated with functional MM imaging, which involves the detection of oxygen consumption in various parts of a brain by measuring the increase in blood flow required to sustain it. The present approach is believed to be more efficient, cheaper, and faster, and should prove particularly valuable as an alternative methodology where a fast, noninvasive, imaging method to detect oxygen consumption in living organisms is desirable.

It is believed that should it be established that the RF waves emitted have relevance on neuronal function in the same way or similar to the ways discussed with respect to cell respiration, the present methodology shall have obvious application in genetically mapping, diagnosing, repairing and/or identifying brain function. For example, insofar as the emitted radiofrequency signals reflect brain activity, the proposed approach may be used to monitor the functional state of the brain much as the EEG is used today.

Anesthesia monitoring, which is currently achieved by measuring spectral parameters of the EEG, may be performed using the proposed approach. RF emission readings may control external devices, as in for example, the automated control of anesthesia.

Where signals are consciously or unconsciously controlled by the subject producing them, the same signals could also be used to control external devices such as computer interfaces, pointers, keyboards, switches and in general any digital or analog input device. The proposed approach ultimately thus can serve as a brain-computer interface for controlling devices or instruments directly or indirectly based on emitted RF signals, either raw or processed.

In view of this disclosure, it is noted that the methods and apparatuses can be implemented in keeping with the present teachings. Further, the various components, materials, structures, and parameters are included by way of illustration and example only and not in any limiting sense. In view of this disclosure, the present teachings can be implemented in other applications and components, materials, structures, and equipment needed to implement these applications, while remaining within the scope of the appended claims.

Those of skill in the art would understand that information and signals may be represented using any of a variety of different technologies and techniques. For example, data, instructions, commands, information, signals, bits, symbols, and chips that may be referenced throughout the above description may be represented by DC voltages, currents, RF voltage waveforms and corresponding electric fields, or any combination thereof.

Those of skill would further appreciate that the various illustrative logical blocks, modules, circuits, and algorithm steps described in connection with the embodiments disclosed herein may be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the exemplary embodiments of the invention.

The various illustrative logical blocks, modules, and circuits described in connection with the embodiments disclosed herein may be implemented or performed with a general-purpose processor, a Digital Signal Processor (DSP), an Application Specific Integrated Circuit (ASIC), a Field Programmable Gate Array (FPGA) or other programmable logic device, discrete gate or transistor logic, discrete hardware components, or any combination thereof designed to perform the functions described herein. A general-purpose processor may be a microprocessor, but in the alternative, the processor may be any conventional processor, controller, microcontroller, or state machine. A processor may also be implemented as a combination of computing devices, e.g., a combination of a DSP and a microprocessor, a plurality of microprocessors, one or more microprocessors in conjunction with a DSP core, or any other such configuration.

The steps of a method or algorithm described in connection with the embodiments disclosed herein may be embodied directly in hardware, in a software module executed by a processor, or in a combination of the two. A software module may reside in Random Access Memory (RAM), flash memory, Read Only Memory (ROM), Electrically Programmable ROM (EPROM), Electrically Erasable Programmable ROM (EEPROM), registers, hard disk, a removable disk, a CD-ROM, or any other form of storage medium known in the art. An exemplary storage medium is coupled to the processor such that the processor can read information from, and write information to, the storage medium. In the alternative, the storage medium may be integral to the processor. The processor and the storage medium may reside in an ASIC. The ASIC may reside in a user terminal. In the alternative, the processor and the storage medium may reside as discrete components in a user terminal.

In one or more exemplary embodiments, the functions described may be implemented in hardware, software, firmware, or any combination thereof. If implemented in software, the functions may be stored on or transmitted over as one or more instructions or code on a computer-readable medium. Computer-readable media includes both computer storage media and communication media including any medium that facilitates transfer of a computer program from one place to another. A storage media may be any available media that can be accessed by a computer. By way of example, and not limitation, such computer-readable media can comprise RAM, ROM, EEPROM, CD-ROM or other optical disk storage, magnetic disk storage or other magnetic storage devices, or any other medium that can be used to carry or store desired program code in the form of instructions or data structures and that can be accessed by a computer. Also, any connection is properly termed a computer-readable medium.

The previous description of the disclosed exemplary embodiments is provided to enable any person skilled in the art to make or use the present invention. Various modifications to these exemplary embodiments will be readily apparent to those skilled in the art, and the generic principles defined herein may be applied to other embodiments without departing from the spirit or scope of the invention. Thus, the present invention is not intended to be limited to the embodiments shown herein but is to be accorded the widest scope consistent with the principles and novel features disclosed herein.

What is claimed is:

1. A method of passively detecting radiofrequency (RF) signals spontaneously emitted by a non-equilibrium population of electrons that are spin polarized by flowing through a chiral media during relaxation of the spin polarized electrons to equilibrium at a frequency corresponding to a Zeeman spin-flip energy of the spin polarized electrons under influence of a magnetic field (MF), the method comprising:
   applying the MF to the chiral media for a predefined time period to shift a frequency and magnitude of the spontaneously emitted RF signals in line with Zeeman effect; and
   passively detecting and storing the shifted emitted RF signals for medical use applications using a receiver antenna tuned to a resonant frequency of the shifted emitted RF signals.

2. The method of claim 1, wherein the incident MF applied to the chiral medial has a strength of up to 0.6 Tesla and the shifted emitted RF signal detected by the receiver antenna has a frequency of up to 16.8 GHz.

3. The method of claim 1, wherein the receiver antenna is a directional antenna with beam forming characteristics.

4. The method of claim 1, wherein the receiver antenna is tuned as a function of a selected magnitude of the applied incident MF and a desired depth reading.

5. The method of claim 1, wherein the incident MF applied to the chiral medial has a strength in the range of 0.005 Tesla to 0.6 Tesla and the shifted emitted RF signal detected by the receiver antenna has a frequency in the range of 140 MHz to 16.8 GHz.

6. A method of passively detecting spontaneously emitted radiofrequency (RF) signals at a frequency of an order of Zeeman energy created by directing a magnetic field (MF) at spin polarized electrons traveling in chiral media, the method comprising:
   generating and directing the MF at a targeted region of the chiral media to induce the emitted RF signals that are correlated in energy and frequency to the MF without any external energy input; and
   detecting the emitted RF signals using a receiver antenna tuned to a resonant frequency of the emitted RF signals.

7. The method of claim 6, wherein the MF directed to the targeted region has a strength of up to 0.6 Tesla and the detected emitted RF signal has a frequency of up to 16.8 GHz.

8. The method of claim 6, wherein the receiver antenna is a directional antenna with beam forming characteristics.

9. The method of claim 6, wherein the MF directed to the targeted region has a strength in the range of 0.005 Tesla to 0.6 Tesla and the detected emitted RF signal has a frequency in the range of 140 MHz to 16.8 GHz.

10. A method of passively detecting emitted radiofrequency (RF) signals that are spontaneously emitted by a population of electrons that are spin polarized by flowing through chiral media as the spin polarized electrons relax from non-equilibrium to equilibrium while radiating at a frequency, under influence of an external MF, determined by a Zeeman spin-flip energy of the spin polarized electrons, the method comprising:
    selectively generating the external MF having a magnitude that induces spin polarized electrons at a higher state exposed to the external MF to acquire extra energy; and
    directing the external MF at the chiral media in a targeted region to cause a portion of the population of spin polarized electrons exposed to the external MF which acquire extra energy to use that extra energy, without any further external energy input, to radiate at a frequency for detection by a receiver antenna and correlated in frequency to the external MF, in line with Zeeman effect.

11. The method of claim 10, wherein the external MF directed at the chiral medial has a strength of up to 0.6 Tesla and the spin polarized electrons exposed to the external MF radiate at a frequency of up to 16.8 GHz.

12. The method of claim 10, wherein the receiver antenna is a directional antenna with beam forming characteristics.

13. The method of claim 10, wherein the external MF directed at the chiral medial has a strength in the range of 0.005 Tesla to 0.6 Tesla and the spin polarized electrons exposed to the external MF radiate at a frequency in the range of 140 MHz to 16.8 GHz.

14. A device for detecting passively emitted radio frequency (RF) waves generated by electrons traveling in chiral media of flies, comprising:
    a permanent magnet for applying a magnetic field to the chiral media for a predefined time period to shift a frequency and magnitude of the RF waves in line with Zeeman effect;
    a waveguide defined at one end by a chamber configured to contain the flies and tuned to a predetermined operational frequency;
    a low noise amplifier (LNA) coupled to at an opposite end of the chamber;
    a bandpass filter (BPF) centered on the frequency of the permanent magnet and coupled to the output of the LNA;
    a detector coupled to the output of the BPF;
    a lock-in reference signal generator (LRSG) for generating a lock-in reference signal to bias the detector;
    an audio amplifier;
    a signal generator for generating a main reference signal that feeds into both the LRSG and the audio amplifier, where the audio amplifier converts the received main reference signal to an oscillating current signal; and
    a solenoid for receiving the oscillating current signal and modulating it to the frequency of the permanent magnet to produce passively emitted RF waves.

\* \* \* \* \*